United States Patent
Yagihasi et al.

[11] Patent Number: 5,599,949
[45] Date of Patent: Feb. 4, 1997

[54] BISPHENOL DERIVATIVE AND ITS MANUFACTURING METHOD

[75] Inventors: Fujio Yagihasi, Yokohama; Minoru Takamizawa, Setagaya-ku, both of Japan

[73] Assignee: Shin-Etsu Chemical Co., Ltd., Japan

[21] Appl. No.: 462,527

[22] Filed: Jun. 5, 1995

Related U.S. Application Data

[62] Division of Ser. No. 294,214, Aug. 22, 1994.

[30] Foreign Application Priority Data

Aug. 23, 1993 [JP] Japan .................................. 5-229505

[51] Int. Cl.$^6$ .................................................. C07D 307/83
[52] U.S. Cl. ............................................ 549/214; 549/305
[58] Field of Search ........................................ 549/214, 305

[56] References Cited

FOREIGN PATENT DOCUMENTS 2-311473  12/1990  Japan .

OTHER PUBLICATIONS

Cotterill et al, J. Chem. Soc. (G), pp. 1758–1764, 1970.
Greene et al., "Protective groups in Oganic Synthesis", 2nd edition, pp. 10–14, John Wiley & Sons, Inc. 1991.

*Primary Examiner*—Ba K. Trinh
*Attorney, Agent, or Firm*—Millen, White, Zelano, & Branigan, P.C.

[57] ABSTRACT

A bisphenol derivative represented by the following formula and a manufacturing method thereof are disclosed:

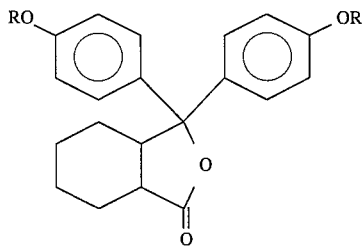

where R is a lower alkyl group, tetrahydropyranyl, methoxymethyl or trialkylsilyl group, and the benzene rings in the formula may be substituted by a lower alkyl group.

6 Claims, No Drawings

BISPHENOL DERIVATIVE AND ITS MANUFACTURING METHOD

This is a division of the application Ser. No. 08/294,214 filed Aug. 22, 1994, pending.

FIELD OF THE INVENTION

This invention relates to a novel bisphenol derivative, in particular to a novel bisphenol derivative that can be used as an intermediate in the synthesis of useful substances and as an indicator of hydrogen ion concentration, and also to a method of manufacturing such a derivative.

BACKGROUND OF THE INVENTION

Conventionally known bisphenol derivatives may be represented by the following formulae,

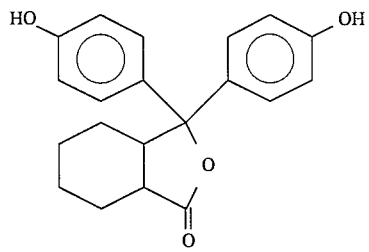

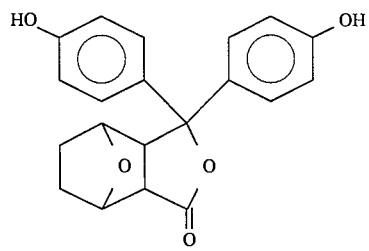

Methods of synthesizing these compounds are described in detail in Vijnana Parishad Anusandhan Patrica 3, 181–4 (1960), Experiencia 14, 257–68 (1958), J. Indian Chem. 40 (9), 785–8 (1963), Ann. Chim. 5, 1165–217 (1960), wherein a condensation reaction is performed between a cyclic acid anhydride and a phenol compounds having a substituent group in the presence of an acid catalyst such as sulfuric acid.

This conventional method, however, suffered from the disadvantages that after synthesizing the phenol compound, a substituent group had to be introduced into the compound, the manufacturing process was long, and a good yield was not obtained.

The inventors, as a result of intensive studies carried out to resolve the above problem, found that the bisphenol derivative of this invention could be obtained in a short process and in high yield by reacting a Grignard reagent derived from a substituted phenol with cyclohexane-1,2-dicarboxylic acid anhydride.

SUMMARY OF THE INVENTION

It is therefore an object of this invention to provide a novel bisphenol derivative which can be used as an intermediate for synthesizing useful substances.

It is a further object of this invention to provide a method of manufacturing such a novel bisphenol derivative by a short process which gives a high yield.

The above objects are attained by a method of manufacturing the aforesaid bisphenol derivative characterized in that a Grignard reagent derived from the substituted phenol represented by the following formula,

is reacted with cyclohexane-1,2-dicarboxylic acid anhydride represented by the following formula,

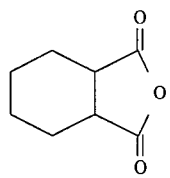

In the above formula, R is a lower alkyl group, tetrahydropyranyl, methoxymethyl or trialkylsilyl, the benzene ring in the formula may be substituted by a lower alkyl group, and X is a halogen atom.

DETAILED DESCRIPTION OF THE INVENTION

The required Grignard reagent may easily be obtained by the method known in the art for synthesizing Grignard reagents, namely, by reacting the substituted phenol having the formula of

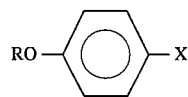

with metallic magnesium in ethyl alcohol or an ether-type solvent such as tetrahydrofuran.

In the above formula, R is a lower alkyl group, tetrahydropyranyl, methoxymethyl or trialkylsilyl, the benzene ring in the formula may be substituted by a lower alkyl group, and X is a halogen atom. As the lower alkyl group, one which has 1–6 carbon atoms is preferable.

The reaction between the Grignard reagent and cyclohexane dicarboxylic acid anhydride may be performed at any temperature from −78° C. to the boiling point of the solvent, however, to obtain the bisphenol derivative in high yield, it is preferably performed at a lower temperature in this range.

The reaction solution obtained is neutralized by an aqueous solution of a common acid such as hydrochloric acid, and after separating the organic layer at a pH of 3 to 5, the product is purified by the usual methods of organic synthesis. This gives the following bisphenol derivative of the present invention.

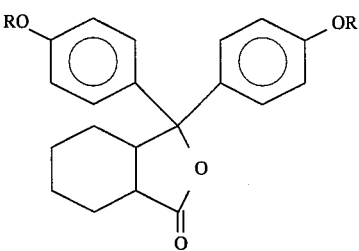

The novel bisphenol derivative of this invention is useful as an additive for modifying polymers, and as an intermediate in the synthesis of physiologically active substances.

In addition, the compound obtained by eliminating the group protecting the phenolic hydroxyl group is also useful as an indicator for showing hydrogen ion concentration in aqueous solutions.

Moreover, if the phenolic hydroxyl group from which the protecting group has been eliminated is substituted by a functional group which can easily be dissociated and eliminated under acidic conditions, the compound exhibits excellent properties as a solution inhibitor for optical resists.

The method of manufacturing the novel bisphenol derivative of this invention makes it possible to obtain the target compound in high yield by means of a short process, and it therefore provides a bisphenol derivative with excellent cost performance. Further, the novel bisphenol derivative so obtained may in particular be used as an intermediate in the synthesis of useful substances, and as a hydrogen ion concentration indicator.

EXAMPLES

This invention will now be described in more detail with reference to specific examples, but it shall be understood that the invention is in no way limited to these embodiments Example 1

A Grignard reagent was prepared by reacting 2.48 g (0.1 mol) of metallic magnesium with 18.5 g (0.1 mol) of p-t-butoxydichlorobenzene in 100 ml of tetrahydrofuran in a nitrogen atmosphere according to the usual method.

7.7 g (0.05 mol) of cyclohexane dicarboxylic acid anhydride was dissolved in 100 ml of tetrahydrofuran, and the solution cooled to 70° C. in dry ice and acetone.

Next, the Grignard reagent prepared as described hereinabove, was slowly dripped into the cooled solution at −70° C. over approximately 30 min, and stirring was then continued at −70° C. for a further 30 min. The temperature of the reaction mixture was then raised to 10° C. on the water bath, and the mixture left overnight.

To the reaction solution obtained, 100 ml of water was slowly added while cooling in ice so as to decompose the Grignard reagent, 1N hydrochloric acid was added to adjust the pH to 3, and the organic layer was separated.

After drying the organic layer with anhydrous sodium sulfate, it was evaporated to give an oily residue. Hexane was added to this oily residue, the mixture was stirred, the crystals produced were filtered and washed with hexane, and then dried to give approx. 5 g of by-product.

After allowing the filtrate to stand, filtering the crystals which separated and drying them, 7.3 g of product was obtained (yield 38% ). The melting point of thee crystals was 171° C. (MeOH), and the measured value of δ in the $^1$HNMR (CDCl$_3$) were as follows:

0.92 (1H, m), 1.07 (2H, m), 1.31 (9H, s), 1.5 (1H, s), 1.6 (2H, m), 2.09 (1H, m), 2.88 (1H, s), 3.07 (1H, m), 6.95 (2H, d), 7.12 (2H, d) and 7.21 (2H, d).

This shows that the compound obtained was a substantially pure bisphenol derivative represented by the following formula.

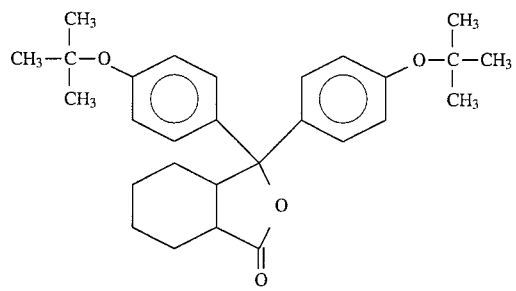

From the remaining solution and chloroform solution dissolved aforesaid, 5 g of crystal obtained as by-product were then subjected to silica gel chromatography using hexane-chlorofom (1:1) as the eluent. This gave a further 3.4 g of product (yield 17.5%), thereby bringing the total yield of compound having the above formula to 55.5%.

The side-product was also analyzed, and found to consist mainly of a substance having the following formula.

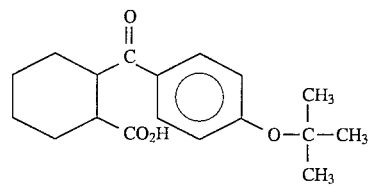

Example 2

A Grignard reagent was prepared and reacted in exactly the same way as that of Example 1, excepting that p-t-tetrahydropyran-2-yl-chlorobenzene was used instead of p-t-butoxydichlorobenzene.

The organic layer was separated from the reaction solution obtained as in Example 1 so as to give an oily residue. This oily residue was separated by silica gel chromatography to give 15.6 g (yield 65%) of colorless crystals of the desired reaction product.

The measured values of δ in the $^1$HNMR (CDCl$_3$) for the crystals obtained were as follows:

3.6 (6H, m), 3.8 (6H, m), 5.3 (4H, m), 6.0 (2H, m), 7.0 (4H, d) and 7.2 (4H, d), confirming that the product was a substantially pure bisphenol derivative represented by the following formula.

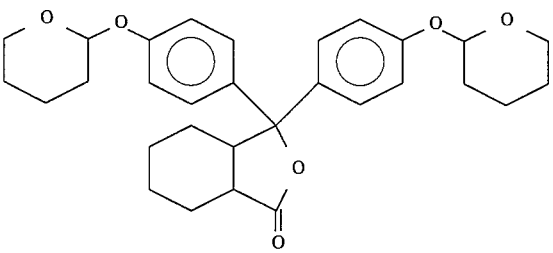

Example 3

A reaction was performed in exactly the same way as in Example 1, excepting that p-t-(t-butyldimethylsilyloxy)bromobienzene was used instead of p-t-butoxydichlorobenzene. The product obtained was purified by silica gel chromatography to give 13.4 g (yield 54%) of a bisphenol derivative represented by the following formula.

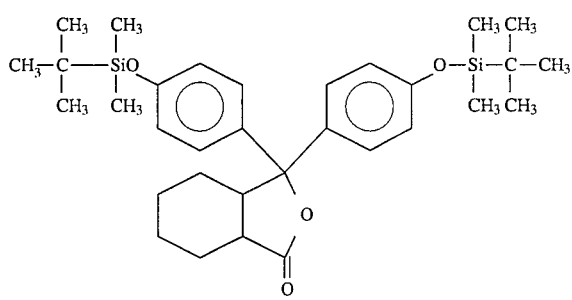

The structure of the compound was confirmed by $^1$HNMR (CDCl$_3$). The measured values of δ were as follows:

0.08 (6H, s), 0.88 (9H, s), 2.08 (1H, d), 2.75 (1H, t), 3.20 (1H,m), 7.11 (2H, d), 7.15 (2H, d), 7.35 (2H, d) and 7.54 (2H, d).

What is claimed:

1. A method of manufacturing a bisphenol derivative of the following formula

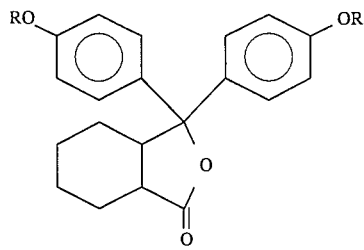

where R is a lower alkyl group, tetrahydropyranyl, methoxymethyl or trialkylsilyl group, and the benzene rings in the formula are optionally substituted by a lower alkyl group, which comprises reacting a Grignard reagent derived from the following substituted phenol

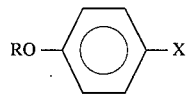

with cyclohexane-1,2-dicarboxylic acid anhydride; where R is as defined above, and X is halogen.

2. A method as claimed in claim 1, wherein the reaction is carried out at temperature from −78° C. to the boiling point of a solvent.

3. A method as claimed in claim 2, wherein the temperature is about −70° C.

4. The method of claim 1, wherein the yield of the bisphenol derivative product is at least 54%.

5. The method of claim 1, wherein R is a lower alkyl group of 1–6 carbon atoms.

6. The method of claim 1, wherein benzene rings in the bisphenol derivative product are substituted with lower alkyl groups.

* * * * *